United States Patent [19]

Sanzo et al.

[11] Patent Number: 5,134,065
[45] Date of Patent: Jul. 28, 1992

[54] TISSUE PLASMINOGEN ACTIVATOR INHIBITOR AND METHOD OF PURIFICATION

[75] Inventors: Michael A. Sanzo, St. Louis; Arthur J. Wittwer, Ellisville; Jayne C. Marasa; Joseph Feder, both of St. Louis, all of Mo.

[73] Assignee: Monsanto Company, St. Louis, Mo.

[21] Appl. No.: 864,070

[22] Filed: May 16, 1986

[51] Int. Cl.$^5$ .................. C12P 21/00; C12N 9/50; C12N 9/72; C12N 9/64
[52] U.S. Cl. .................. 435/703; 435/215; 435/212; 435/219; 435/226; 530/380; 530/413; 530/414; 530/416; 530/417
[58] Field of Search .......... 530/380, 381, 344, 350, 530/402, 409, 413, 414, 416, 417, 849; 435/68, 70, 240.2, 215, 216, 226, 70.3

[56] References Cited

U.S. PATENT DOCUMENTS 3,778,352 12/1973 Bishop et al. ............... 195/99
4,661,453 4/1987 Pollard ....................... 435/212

OTHER PUBLICATIONS

The EMBO Journal, vol. 5, No. 10, pp. 2539–2544 (1986).
Ny et al. Proc. Natl. Acad. Sci. USA, 83, 6776–6780 (1986).
Emeis et al., Biochem. Biophys. Res. Commun. 110(2), 392–398 (1983).
Scott et al., J. Biol. Chem. 260(11), 7029–7034 (1985).
Loskutoff et al., Proc. Natl. Acad. Sci. USA 80, 2956–60 (1983).
van Mourik et al., J. Biol. Chem. 259 (23), 14914–21 (1984).
Hekman et al., Ibid. 260(21), 11581–87 (1985).
Lecander et al., Brit. J. Haematol. 57, 407–12 (1984).
Astedt et al., Thromb. Haemostas, 53(1), 122–25 (1985).
Vasalli et al., J. Exp. Med. 159, 1653–68 (1984).
Levin, Proc. Natl. Acad. Sci. USA 80, 6804–08 (1983).
Sprengers et al., Biochim. Biophys. Acta 801, 163–170 (1984).
Philips et al., Ibid. 802, 99–110 (1984).
Pannekoek, J. Cell. Biochem. Supp. 10A, Absts. 15th Ann. Meeting, UCLA Symposium on Mol. & Cell. Biology, Jan. 20–Feb. 15, 1986, Abst. E119, p. 277.
Loskutoff, Ibid. Abst. E5, p. 231.
Levin, "Latent tissue plasminogen activator produced by human endothelial cells in culture: Evidence for an enzyme–inhibitor complex", PNAS, V. 80, 6804–08, 1983.
Philips et al., "Human Endothelial Cells Produce a Plasminoger Activator Inhibitor and a Tissue-Type Plasminogen Activator-Inhibitor Complex", Biochimira et Biophysica Acta, v. 802, 99–110, 1984.
Sprengers et al., "Evidence for the Presence of two Different Fibrinolytic Inhibitors In Human Endothelial Cell Conditioned Medium" Biochim. Biophys. Acta 801, 163–170, 1984.

*Primary Examiner*—John Doll
*Assistant Examiner*—Gail Poulos
*Attorney, Agent, or Firm*—Scott J. Meyer

[57] ABSTRACT

A novel and unique plasminogen activator inhibitor fragment is obtained from human umbilical vein endothelial cells which has the following characteristics:

A. it is derived from a native t-PA inhibitor that binds to and inhibits the activity of t-PA,
B. it is dissociated from a complex formed between said native t-PA inhibitor and t-PA, said complex existing in two distinct interconvertible conformations with molecular weight of about 88 KDa and 105 KDa, respectively, and being partially reversible in the presence of fibrin,
C. it has a molecular weight of about 40 KDa when dissociated from the complex, and
D. it has a novel partial N-terminal amino acid sequence when dissociated from the complex.

1 Claim, 3 Drawing Sheets

ELECTROPHORETIC PROFILE OF HUE CM FRACTIONS

DISSOCIATION OF tPA-INHIBITOR COMPLEXES WITH AMMONIUM HYDROXIDE (NONREDUCED GEL)

TISSUE PLASMINOGEN ACTIVATOR INHIBITOR AND METHOD OF PURIFICATION

BACKGROUND OF THE INVENTION

This invention relates to a fibrinolytic inhibitor and, more particularly, to a plasminogen activator inhibitor fragment derived from human umbilical vein endothelial cells.

The plasminogen activators are a class of serine proteases that convert plasminogen to the fibrinolytically active enzyme plasmin (fibrinolysin). Upon being thus activated, the plasmin can attack the coagulation proteins of the fibrin clot (thrombus) and thereby disintegrate the clot. Inhibitors normally present in the blood with plasminogen generally retard this reaction. Most of the plasminogen activator in human plasma exists in the form of an enzyme-inhibitor complex (EI).

Human plasma contains two plasminogen activators that are immunologically distinct, namely tissue plasminogen activator (t-PA) and urokinase (UK). t-PA has been demonstrated to have higher affinity for fibrin than UK and, therefore, is a preferable agent for degradation of the fibrin clot. The source of the plasma t-PA has been presumed to be the vascular endothelium and it has been shown that endothelial cells are associated with plasminogen activator activity. Fibrinolytic inhibitors also have been found in human endothelial cell extracts. See, for example, Emeis et al., Biochem. Biophys. Res. Commun. 110(2) 392-398 (1983).

Although it has been established that plasminogen activator inhibitors are present in endothelial cells, highly purified and characterized isolates of these inhibitors or inhibitor fragments are not believed to have been reported prior to the present invention. Availability of such a purified inhibitor from endothelial cells would be useful for regulation of the fibrinolytic reaction. For example, when the administered dose of plasminogen activator turns out to be greater than biologically required to disintegrate the clot, the excess plasminogen acting on circulating fibrinogen. In such instances, the plasminogen activator inhibitor could be given after administration of t-PA or UK to reduce the fibrinogenolysis caused by any excess plasminogen activator. The risk of hemorrhage would thereby be reduced.

Plasminogen activator inhibitors have been obtained from various sources. The best characterized of these inhibitors, known as protease nexin, was isolated from cultured human fibroblasts and has an apparent $M_r$ of about 43 kilodaltons (KDa). Scott et al., J. Biol. Chem. 260(11), 7029-7034 (1985). It is distinguished by its acid lability, its ability to inhibit both plasminogen activators and plasmin, its relatively high pI (7.5-7.8) and by the stimulatory effect of heparin on its activity.

Plasminogen activator inhibitor also has been partially purified from bovine aortic endothelial cells and has been reported to have a $M_r$ of about 50,000 (50 KDa). Loskutoff et al., Proc. Nat. Acad. Sci. USA 80., 2956-2960 (1983); van Mourik et al., J. Biol. Chem. 259(23), 14914-14921 (1984); and Hekman et al., Ibid. 260 (21), 11581-11587 (1985).

A placental type inhibitor having a $M_r$ of about 50,000 and a pI of about 4.8-4.9 has been described by Lecander et al., Brit. J. Haematol. 57, 407-412 (1984); and Astedt et al., Thromb. Haemostas. 53(1), 122-125(1985). It inhibits t-PA and UK but not plasmin, and it appears to be immunologically distinct from inhibitors found in endothelial cells. The same inhibitor is produced by monocytes and macrophages. See, for example, Vassalli et al., J. Exp. Med. 159, 1653-1668(1984).

Various reports on plasminogen activator inhibitor in human umbilical endothelial cells have been published by Emeis et al., Biochem. Biophys. Res Commun. 110(2), 392-398(1983); Levin, Proc. Nat. Acad. Sci. USA 80, 6804-6808 (1983); Sprenger et al., Biochim. Biophys. Acta 801, 163-170 (1984); Philips et al., Ibid. 802, 99-110 (1984); and other scientists. The molecule acts on t-PA and UK but not on plasmin. It is acid stable and has a $M_r$ of about 50 KDa prior to binding to protease.

Recently, it was reported that a heterologous antiserum was raised against bovine endothelial plasminogen activator inhibitor and used to screen a human endothelial cDNA expression library in E coli. A cDNA insert of an antigen-producing clone was found to hybridize with a human endothelial mRNA, and a synthetic oligonucleotide derived from the insert was used to detect homologous clones. DNA sequencing revealed that the cloned cDNA's had a striking homology with members of the serine protease inhibitor family, namely antithrombin III, $\alpha_2$-antiplasmin and $\alpha_1$-antitrypsin. Pannekoek, J. Cell. Biochem. Supp. 10A, Absts. 15th Ann. Meeting, UCLA Symposia on Molecular & Cellular Biology, Jan. 20-Feb. 15, 1986, Abst. E119, p. 277. At the latter meeting it was also reported that the plaminogen activator inhibitor gene from bovine aorta endothelial cells was cloned and sequenced. Loskutoff, Ibid. Abst. E5, p. 231.

BRIEF DESCRIPTION OF THE INVENTION

In accordance with the present invention, a highly purified plasminogen activator inhibitor fragment is provided which has the following characteristics:

A. it is derived from a native t-PA inhibitor that binds to and inhibits the activity of t-PA, B. it is dissociated from a complex formed between said native t-PA inhibitor and t-PA, said complex existing in two distinct interconvertible conformations with molecular weight of about 88 KDa and 105 KDa,respectively, and being partially reversible in the presence of fibrin, C. it has a molecular weight of about 40 KDa when dissociated from the complex, and D. it has a partial N-terminal amino acid sequence when dissociated from the complex as follows:

$$\overset{1}{\text{Met}}—\text{Ala}—\text{Pro}—\text{Glu}—\text{Glu}—\text{Ile}—\text{Ile}—\text{Met}—\text{Tyr}—\text{Arg}—$$

$$\text{Pro}—\text{Phe}—\text{Leu}—\text{Phe}—\text{Val}—\text{Val}—\text{X}—\text{Trp}—\overset{19}{\text{Asn}},$$

wherein amino acid X is not determined.

The plasminogen activator inhibitor fragment defined herein is believed to be a novel and unique protein. No protein with the foregoing amino acid sequence and combination of properties is believed to have been described heretofore. The fragment can be used for generating antibodies against itself and against the native t-PA inhibitor. These antibodies have potential use as diagnostics and therapeutics for patients with cardiovascular diseases. The antibodies also can be used for purifying the native form of the t-PA inhibitor. The amino acid sequence defined herein can be used to make probes for the cloning of the gene which codes for the native t-PA inhibitor. An advantage of the native inhibitor with activity which is partially reversible in the presence of fibrin consists in its ability to permit administered t-PA to act upon fibrin emboli while at the same time reducing the total systemic activity of the t-PA. Thus, this type of inhibitor could be administered with less risk of generating thromboembolisms than an inhibitor with irreversible activity. Although the inventors are not bound by theory, it is believed that the ability to change the conformational form of the t-PA-inhibitor complex may have an effect on its rate of dissociation in the presence of fibrin or on its rate of clearance from the body.

The plasminogen activator inhibitor fragment as defined above has been purified to homogeneity as a complex from human umbilical vein endothelial cells grown in nutrient culture medium. That is, it has been prepared in a form which is essentially free of other proteins, cellular components, and tissue matter with which it is found in the native state. The cells were isolated from human umbilical cord tissue and placed in in vitro culture. They were maintained in confluent cultures from which the conditioned media was obtained and used to isolate the t-PA-inhibitor complex that was then used as a source of the t-PA inhibitor fragment. The inhibitor fragment was dissociated from the complex and purified by high performance liquid chromatography (HPLC) on gel filtration (size exclusion) type columns.

DETAILED DESCRIPTION OF THE INVENTION

Figure 1:
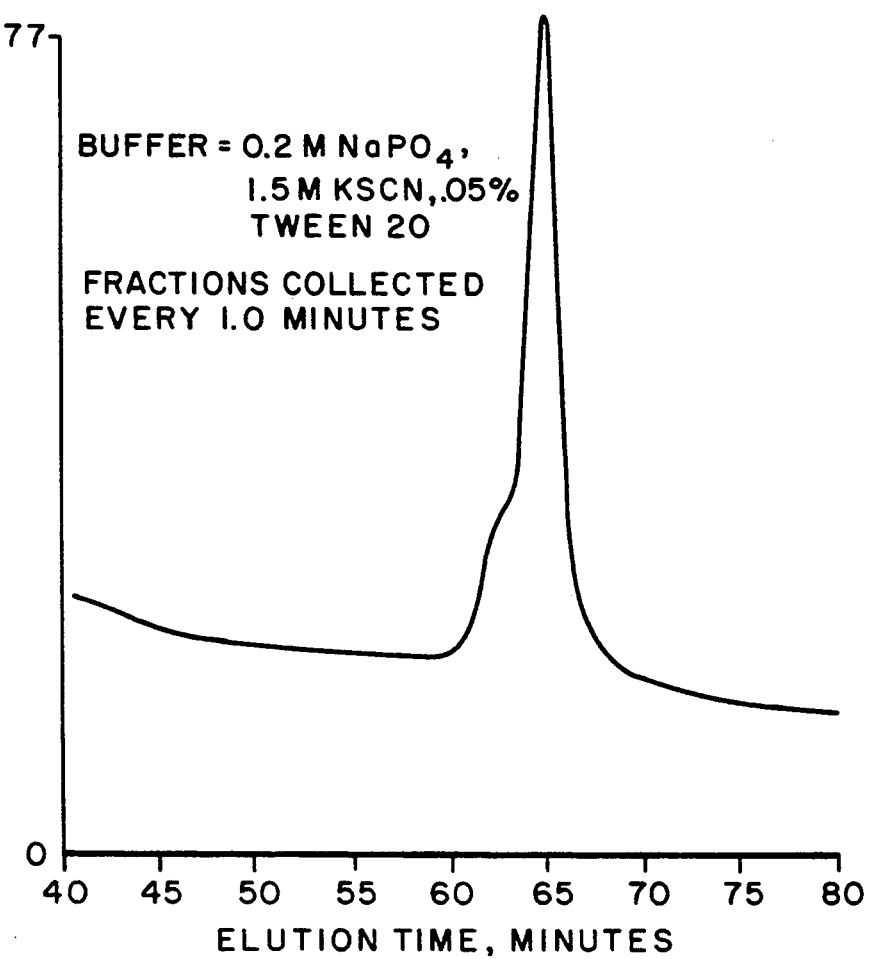

While the specification concludes with claims particularly pointing out and distinctly claiming the subject matter regarded ar forming the present invention, it is believed that the invention will be better understood from the following description of the preferred embodiments taken in conjunction with the accompanying drawings in which:

FIG. 1 is a graphical representation which shows the high performance liquid chromatography (HPLC) elution profile (Absorption at 280 nm) in one embodiment of the invention. In this embodiment, the t-PA inhibitor complex derived from the conditioned media (CM) of cultured human umbilical endothelial cells (HUE) is adsorbed on PAM 2-Sepharose, eluted with buffer, and the eluant fractions which exhibit t-PA antigenic activity in a t-PA ELISA assay are then pooled, concentrated by ultrafiltration, and applied to HPLC gel filtration columns.

Figure 2:
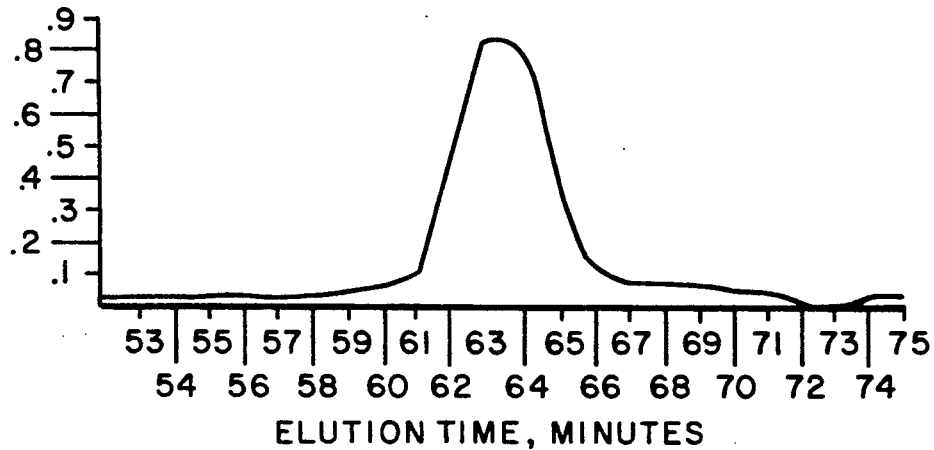

FIG. 2 is a graphical representation which shows the t-PA enzyme linked immunosorbent assay (ELISA) elution profile (Absorption at 490 nm) of the PAM 2-Sepharose eluant fractions of FIG. 1.

Figure 3:
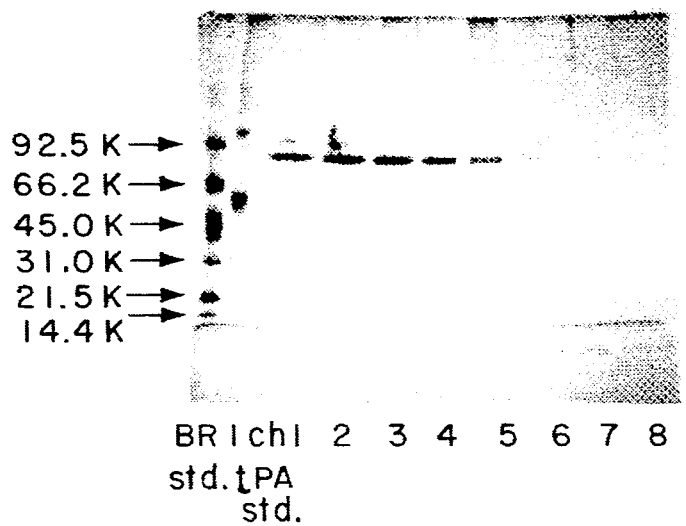

FIG. 3 shows the electrophoretic profile of the HPLC fractions of FIG. 1 in which the fractions were examined on a 5-15% Laemmli non-reduced gel. Lanes 1 to 8 show the fractions collected at 61 to 68 minutes, respectively, in FIG. 1. The control lanes are Bio-Rad ® (BR) molecular weight standards (14.4-92.5 KDa) obtained from Bio-Rad Laboratories and a single chain (1 ch) t-PA standard obtained from American Diagnostica Incorporated.

Figure 4:
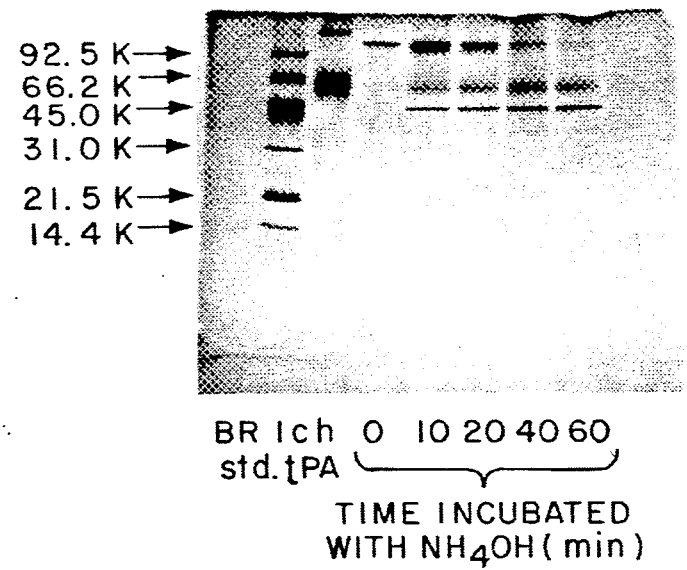

FIG. 4 shows the dissociation of the t-PA inhibitor complex with ammonium hydroxide as examined on a 10-20% Laemmli non-reduced gel. Five 100 µl samples of fraction 65 from FIG. 1, each treated with 100 µl 3M $NH_4OH$, were incubated in a water bath at 37° C. for 0, 10, 20, 40 and 60 minutes, respectively. At the end of these intervals, the samples were removed from the incubator, neutralized with HCl, treated with 1.0 ml buffer, concentrated and examined by the stated electrophoresis method.

Figure 5:
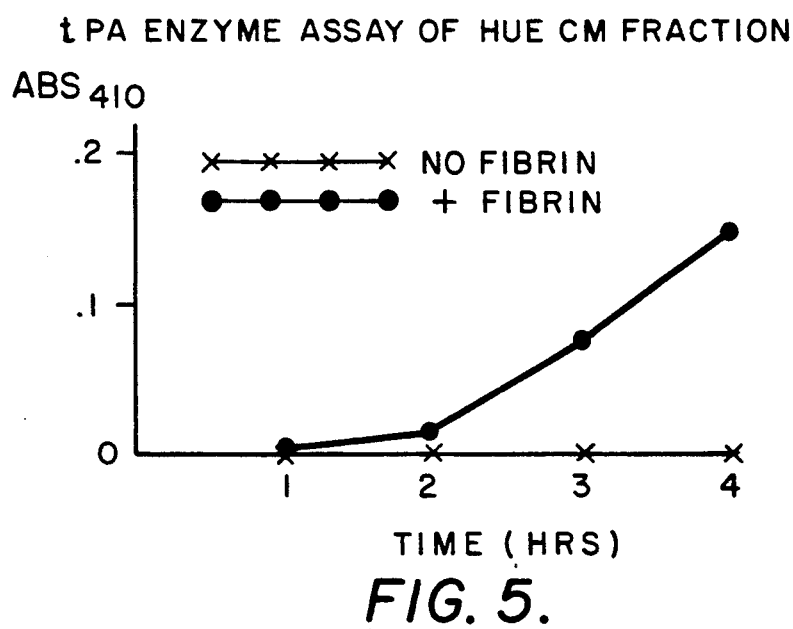

FIG. 5 is a graphical representation which shows the t-PA enzymatic assay of the t-PA inhibitor complex from a representative HPLC eluant fraction in another embodiment of the invention. The t-PA enzymatic assay (Absorption at 410 nm) was carried out both in the presence and absence of fibrin.

The electrophoresis system used in these figures was a conventional Laemmli SDS-PAGE system (sodium dodecylsulfate polyacrylamide gel electrophoresis), such as described by Laemmli, Nature 227, 680–685 (1970). The Bio-Rad molecular weight standards used in this electrophoresis were as follows:

| Mol. wt. | Protein | Reference |
| --- | --- | --- |
| 14,400 | Lysozyme | Jolles, Angew. Chem. Intl. Ed. 8, 227 (1969). |
| 21,500 | Soybean Trypsin Inhibitor | Wu and Scheraga, Biochemistry 1, 698 (1962). |
| 31,000 | Carbonic Anhydrase | Davis, in The Enzymes, Vol. V, p. 545, Boyer, Ed. Academic Press, N.Y., 1971. |
| 45,000 | Ovalbumin | Warner, in The Proteins, Vol. 11A, p. 435, Neurath and Bailey, Eds., Academic Press, N.Y., 1954. |
| 66,200 | Bovine Serum Albumin | Brown, Fed. Proc. 34, 591 (1975). |
| 92,500 | Phosphorylase B | Seery et al., Biochemistry 6, 3315 (1967). |

The endothelial cells used herein are initially isolated from human umbilical cord veins and propagated in conventional culture media. The primary tissue is originally obtained from conventional surgical procedures and the cells are isolated therefrom and cultured essentially by established methodology such as described by Jaffe, Transplantation Proc. 12(3), Supp. 1, 49–53 (1980); Knedler and Ham, In Vitro, 19(3), 254 (1983); Gimbrone, Prog. in Haemostas. and Thromb., T. H. Spaet ed., Grune and Stratton, Inc., N.Y., 1976, pp. 1–28.

The thus obtained endothelial cells are preferably grown in a humidified atmosphere at 37° C. with a 5–7% $CO_2$ overlay for at least about 12 hours and preferably for about 18–24 hours. The cells can be routinely grown in T-Flasks to confluency or in other standard cell culture apparatus. The flask culture surface preferably is coated with fibronectin. The cells can thus be cultured in Medium 199, DMEM, RPMI 1640 medium and other such well-known culture media as described, for example, by H. J. Morton, In Vitro 6, 89–108 (1970); and Jayme and Blackman, Adv. Biotech. Proc. 5, 1–30 (1985), Eds. Mizrahi and van Wezel, Alan R. Liss, Inc., New York. These conventional culture media contain known amino acids, mineral salts, vitamins, hormones and carbohydrates. They are also frequently fortified with mammalian sera such as fetal bovine sera.

Illustratively, the endothelial cells have been routinely cultured in Medium 199 (Gibco) supplemented with 10% fetal bovine serum, 90 µg/ml heparin, sodium salt, 1 µg/ml hydrocortisone, 10 ng/ml epidermal growth factor (EGF - Collaborative Research), 30 µg/ml endothelial cell growth supplement (ECGS Collaborative Research) and 100 µg/ml gentamicin. The cells also have been cultured in Dulbecco's Modified Eagle's Medium (DMEM) and other such media similar to the culture of bovine endothelial cells as described by Olander et al, *In Vitro* 18(2), 99–107 (1982).

The endothelial cells used herein can be grown in either serum-free or serum-containing media, although the media preferably contains added sera, for example, 5-20% fetal bovine serum. It was unexpectedly found that greater levels of the inhibitor are produced in the serum-containing medium. Serum itself contains various extraneous inhibitors which tend to suggest avoidance of its use in media for production of desired inhibitors under cell culture conditions. However, the amount of extraneous inhibitor contributed by the serum is relatively small compared to the amount of the desired inhibitor produced by the endothelial cells. Therefore, untreated commercially available mammalian serum can be used in the culture medium. Nevertheless, serum which has been pre-treated with acid to destroy inhibitors also can be used, if desired. The serum thus can be acidified to a pH of about 3 with HCl, incubated at about 37° C. for about one hour and then adjusted to a pH of about 7.4 before use. This acid treatment destroys most of the endogenous inhibitory activity present in the serum.

It has been found that the conditioned medium from the culture of the endothelial cells has no measurable t-PA enzymatic activity, but has t-PA antigenic activity, thus indicating that the inhibitor level is in excess of the t-PA level.

Isolation and purification of the desired t-PA inhibitor fragment from the conditioned media preferably is carried out by the following method:

A. adsorbing the t-PA inhibitor complex on PAM 2-Sepharose ® and eluting the complex with a stepwise or gradient elution buffer containing 1-2M KSCN, B. optionally but preferably concentrating the eluant fractions which exhibit t-PA antigenic activity by ultrafiltration, C. sieving the eluant fractions or concentrated eluant fractions on HPLC gel filtration columns, D. dissociating the concentrated, purified complex by incubating in ammonium hydroxide, E. neutralizing the resulting incubate with acid, and then F. isolating the inhibitor fragment by rechromatographing the neutralized incubate on HPLC gel filtration columns.

The thus obtained purified inhibitor fragment is a single chain protein with a molecular weight of about 40 KDa as determined by polyacrylamide gel electrophoresis on sodium dodecylsulfate (SDS) gels.

The PAM 2-Sepharose used in step A, above, is an immunoaffinity chromatographic material consisting of monoclonal antibodies to two-chain t-PA from Bowes melanoma immobilized on Sepharose-4B (bead-formed agarose gel) matrix commercially available from American Diagnostica Incorporated (ADI), Greenwich, Conn. Following adsorption of the t-PA inhibitor complex on this material, the column is preferably washed with phosphate buffered saline (PBS, 0.01–0.02M sodium phosphate, 0.15M NaCl, pH 6.8–7.4) containing about 0.05% Tween ®20 (polysorbate 20) or about 0.01% Tween 80 (polysorbate 80) and about 0.25M KSCN. The inhibitor complex is then eluted with a similar buffer containing about 1-2M KSCN.

The ultrafiltration in step B, above, can be conveniently carried out with an Amicon ® YM 30 membrane which has a molecular weight cut-off of about 30,000, and other such conventional ultrafiltration membranes.

A preferred HPLC gel filtration column for use in steps C and F, above, is the DuPont Zorbax ® GF 250 HPLC column which contains a silica support having a 4 micron particle size and a 150 Å pore size. Use of three such columns linked together in series is preferred. After application of the inhibitor-containing material to the column, the column is preferably eluted with a phosphate buffer containing 0.02M $NaH_2PO_4$ (pH 6.8), 1.5M KSCN and 0.05% Tween 20. In step F, 1M ammonium bicarbonate solution with 0.05% Tween 20 can be used instead of the phosphate buffer.

Another suitable HPLC gel filtration column is the commercially available TSK - G3000SW column of Toyo Soda Manufacturing Co., Ltd., Japan.

The purified complex is preferably dissociated into its component proteins in step D, above, by incubation at about 37° C. for about one hour in about 1.5M $NH_4OH$. Hydroxylamine, which has been used by other scientists for dissociating inhibitor complexes, had little effect in promoting dissociation of the present complex unless the preparation was first boiled.

After dissociation in $NH_4OH$, the preparation is brought to neutral pH preferably with HCl in step E.

The following examples will further illustrate the invention in greater detail although it will be appreciated that the invention is not limited to these specific examples.

EXAMPLE 1

Endothelial cells obtained from human umbilical cord veins were grown to confluency in T-flasks in a humidified atmosphere at 37° C. with a 5-7% $CO_2$ overlay in Medium 199.

Cell culture runs were made both in serum-free medium and in medium fortified with 10% fetal bovine serum which was pre-treated by acidification to pH 3 with HCl followed by incubation at 37° C. for one hour and then readjusted to pH 7.4 with NaOH before use in the cell culture medium.

Enzyme Linked Immunosorbent Assays (ELISA) conducted after the cell culture period of 24 hours in a typical run indicated that the serum-free conditioned medium had 49 ng t-PA/ml whereas the serum-containing conditioned medium had 83.9 ng t-PA/ml. A commercially available ELISA kit from ADI and sold under the trademark "Imubind" was used for this assay. This kit contains polyclonal antibodies against t-PA from human uterus which are employed according to conventional ELISA methodology following the double antibody sandwich assay principle. See, e.g., Engvall and Perlmann, *Immunochem.* 8, 871–874(1971).

The conditioned medium was subjected to PAM 2-Sepharose immunoaffinity chromatography to extract the t-PA inhibitor complex. In one run, extraction of the serum-free conditioned medium proceeded during the cell culture period for 24 hours at 37° C. The extract was collected and the PAM 2-Sepharose was pelleted by centrifugation. The pellet was washed with phosphate buffered saline containing 0.05% Tween 20 (Buffer A) and packed in a 1.0 cm inside diameter column. The column was washed with Buffer A containing 0.25M KSCN and a gradient was then run to Buffer A containing 1.2M KSCN. A t-PA ELISA scan was performed on gradient eluted fractions and the active fractions were pooled, concentrated by ultrafiltration and examined by electrophoresis on a 5-15% Weber- Osborn gel under nonreduced conditions [Weber and Osborn, *J. Biol. Chem.* 244(16), 4406-4412 (1969)]. Two prominent bands were observed in the preparation, one with a molecular weight of about 105 KDa, and the other with a molecular weight of about 67 KDa. The higher molecular weight band is due to the t-PA inhibitor complex while the lower molecular weight band is due to free t-PA.

In another run, following the initial cell culture period of 24 hours at 37° C., the serum-free conditioned medium was incubated with PAM 2-Sepharose for 4 hours at room temperature (ca. 20–22° C.) with constant mixing. The PAM 2-Sepharose was then collected by filtration and packed in a column. The column was washed with Buffer A containing 0.25M KSCN and then eluted with a gradient to Buffer A containing 2.0M KSCN. In this run, 2 liter batches of conditioned medium were processed and the resulting fractions examined for t-PA activity using the ELISA assay. Active fractions were pooled and concentrated by ultrafiltration. PAM 2-Sepharose was added to the concentrate which was then slowly diluted with Buffer A to ten times its original volume. After incubating for four hours, the PAM 2-Sepharose was collected and eluted as above. Fractions showing activity in the t-PA ELISA assay were pooled, concentrated by ultrafiltration and applied to three linked DuPont GF 250 HPLC columns (9.4 mm×25 cm). An elution Buffer B consisting of 0.02M NaH$_2$PO$_4$ (pH 6.8), 1.5M KSCN, and 0.05% Tween 20 was applied to the column at a rate of 0.5 ml/min and the effluent was monitored at 280 nm with fractions collected every minute. The absorbance profile showed a broad peak with a shoulder on the left side. Fractions collected at various points along the peak were examined by electrophoresis. The electrophoresis pattern shown by the different fractions was identical, thus demonstrating that the shoulder is due to one protein (t-PA inhibitor complex) that can assume two conformations and not due to two different proteins (or two different complexes). See FIGS. 1-3 for these results. Active fractions from the above run were incubated in 1.5M NH$_4$OH at 37° C. for various time intervals up to one hour with a progressive elimination of the high molecular weight t-PA inhibitor complex and the appearance of two major bands: one with a molecular weight of about 40 KDa (the inhibitor fragment) and the other with a molecular weight indicative of free t-PA (ca. 60 KDa). See FIG. 4 for results with illustrative fraction 65.

Similar extraction runs as above with PAM 2-Sepharose were made with the serum-containing conditioned media with substantially similar results.

EXAMPLE 2

Two additional runs were made for the isolation and purification of the t-PA inhibitor complex as in Example 1, above, one from the serum-containing conditioned medium and the other from the serum-free conditioned medium. Several of the eluant fractions of the complex eluted in the HPLC step were subjected to t-PA enzymatic analysis in the presence and absence of fibrin. In every case, an increase in t-PA activity was observed in the presence of fibrin. These results confirm that the complex is partially reversible in the presence of fibrin and dissociates to form active t-PA. FIG. 5 is illustrative of these results which show the increase in t-PA activity (increase in absorption) during an incubation period of several hours. The t-PA enzymatic analysis was carried out with a commercially available kit from ADI sold under the trademark "Spectrolyse." The assay is based on the functional parabolic rate assay described by Ranby et al., *Thromb. Res.* 27, 743-749 (1982), as adapted to plasma samples disclosed by Wiman et al., *Clin. Chim. Acta* 127, 279-288 (1983).

EXAMPLE 1

Another portion of the t-PA inhibitor complex prepared in Example 1 from the serum-free conditioned media was tested for its interconvertibility between two molecular weight conformations. The complex was first incubated for 24 hours at 37° C. at pH 8.0, pH 6.8 and pH 6.8 in the presence of 5 mM dithiothreitol (DTT) and samples were then subjected to SDS electrophoresis. It was seen that the pH 8.0 incubation resulted in an intensification of the 85 KDa form of the complex, whereas the incubation at 6.8 resulted in the prevalence of the 105 KDa species. In the presence of DTT, the 85 KDa species was almost completely eliminated. In a further test, both the pH 8.0 and pH 6.8 incubations were carried out for 48 hours. At the pH 8.0 incubation the 85 KDa species predominated slightly. The pH 6.8 incubation produced a clear predominance of the 105 KDa band. After 48 hours in the presence of 5 mM DTT, it was seen that most of the complex dissociated into t-PA and a free inhibitor fragment.

EXAMPLE 4

After purification of active fractions from the PAM 2-Sepharose columns by HPLC on G250 columns, complexes from both the serum-containing and serum-free preparations were dissociated by incubation in 1.5M NH$_4$OH as in Example 1. The t-PA inhibitor fragment was then isolated by application to three DuPont GF 250 HPLC columns linked together in series, and eluted with Buffer B as in Example 1. The highly purified fractions were subjected to amino acid sequence analysis with the following results:

1
Met—Ala—Pro—Glu—Glu—Ile—Ile—Met—Tyr—Arg—

19
Pro—Phe—Leu—Phe—Val—Val—X—Trp—Asn, wherein X was not determined.

In the amino acid sequence defined herein, the individual amino acids are designated by conventional abbreviations as follows:

| Amino Acid | Abbreviated Designation |
|---|---|
| L-Alanine | Ala |
| L-Arginine | Arg |
| L-Asparagine | Asn |
| L-Glutamic Acid | Glu |
| L-Isoleucine | Ile |
| L-Leucine | Leu |
| L-Methionine | Met |
| L-Phenylalanine | Phe |
| L-Proline | Pro |
| L-Tryptophan | Trp |
| L-Tyrosine | Tyr |
| L-Valine | Val |

The sequence shown is that determined on the inhibitor fragment from the serum-containing conditioned medium. Partial sequence information also was obtained on the inhibitor fragment from the serum-free conditioned medium with identical results in the nine amino acids determined for the latter material. Since the inhibitor fragment was obtained from a complex, the first amino acid, methionine, represents the cleavage point of the protease for the inhibitor.

Various other examples will be apparent to the person skilled in the art after reading the present disclosure without departing from the spirit and scope of the invention. All such further examples are included within the scope of the appended claims.

What is claimed is:

1. A method for producing a purified plasminogen activator inhibitor fragment which has the following characteristics:
   (A) it is derived from a native t-PA inhibitor that binds to and inhibits the activity of t-PA,
   (B) it is dissociated from a complex formed between said native t-PA inhibitor and t-PA, said complex existing in two distinct interconvertible conformations with molecular weight of about 88 KDa and 105 KDa, respectively, and being partially reversible in the presence of fibrin,
   (C) it has a molecular weight of about 40 KDa when dissociated from the complex,
   (D) it has a partial N-terminal amino acid sequence when dissociated from the complex as follows:

1
   Met—Ala—Pro—Glu—Glu—Ile—Ile—Met—Tyr—Arg—

19
   Pro—Phe—Leu—Phe—Val—Val—X—Trp—Asn, wherein amino acid X is not determined, said method comprising culturing human umbilical vein endothelial cells in nutrient culture medium at about 37° C. and recovering said inhibitor therefrom by subjecting the resulting conditioned medium to immunoaffinity chromatography with PAM 2-Sepharose, eluting the absorbed complex of t-PA and inhibitor with an elution buffer containing about 1-2 molar KSCN, optionally concentrating the active eluant fractions by ultrafiltration, sieving the concentrated fractions or the eluant fractions on HPLC gel filtration columns, dissociating the concentrated, purified complex in $NH_4OH$ solution, neutralizing the dissociated complex and isolating the inhibitor fragment by rechromatographing on HPLC gel filtration columns.

* * * * *